(12) United States Patent
Polkus et al.

(10) Patent No.: US 6,435,716 B1
(45) Date of Patent: Aug. 20, 2002

(54) METHOD AND SYSTEM FOR DETERMINING A SOURCE-TO-IMAGE DISTANCE IN A DIGITAL IMAGING SYSTEM

(75) Inventors: Vincent S. Polkus, Delafield; Jon C. Omernick, Wauwatosa; Jonathan C. Boomgaarden, Waukesha; Robert M. Stetz, Oconomowoc, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/576,848

(22) Filed: May 23, 2000

(51) Int. Cl.$^7$ .................................................. A61B 6/08
(52) U.S. Cl. ........................ 378/205; 378/207; 378/197; 378/98.8
(58) Field of Search .................... 378/205, 207, 378/197, 193, 98.8, 162, 166

(56) References Cited

U.S. PATENT DOCUMENTS

| | | | | |
|---|---|---|---|---|
| 4,766,603 A | * | 8/1988 | Okabe et al. | 378/162 |
| 5,870,450 A | * | 2/1999 | Khutoryansky et al. | 378/197 |
| 6,092,928 A | * | 7/2000 | Mattson et al. | 378/205 |

\* cited by examiner

*Primary Examiner*—Robert H. Kim
*Assistant Examiner*—Drew A. Dunn
(74) *Attorney, Agent, or Firm*—Fletcher, Yoder & Van Someren (57) ABSTRACT

A method is provided for determining source-to-image distance (SID) setpoints in a digital imaging system. SID setpoints are determined during a setup and calibration procedure which includes generating radiation beams while varying certain system parameters, such as the radiation source position, and detecting and determining the size of the radiation beams that impact on the digital detector. SID values and a separation gain constant can then be determined based on the calculated sizes of the detected radiation beams and the feedback signals which are representative of the various system parameters that were varied (e.g., source position, etc.) during the setup and calibration procedure. The separation gain constant and the calculated, empirical SID values can then be used to position the radiation source at any user-selected SID based on position sensor feedback signals. The procedure also provides for a calibrated readout of the SID, which can be displayed to a user of the imaging system.

34 Claims, 4 Drawing Sheets

METHOD AND SYSTEM FOR DETERMINING A SOURCE-TO-IMAGE DISTANCE IN A DIGITAL IMAGING SYSTEM

FIELD OF THE INVENTION

The present invention relates generally to digital imaging systems and, more particularly, to a calibration and setup procedure for determining a separation distance between a radiation source and a digital detector in a digital imaging system.

BACKGROUND OF THE INVENTION

The installation and setup procedures for digital imaging systems, such as radiographic diagnostic imaging systems, can be complex and time-consuming. For example, to comply with customer image quality and consistency requirements and various regulatory and safety standards for diagnostic imaging systems, such procedures generally require the determination of a variety of factors, including the accurate positioning of the x-ray source with respect to the x-ray detector. For instance, the determination and establishment of fixed setpoints (or detent positions) for setting the separation distance between the x-ray source and x-ray detector and calibrating the system such that an accurate readout of the separation distance can be obtained often are required procedures. The determination and establishment of this separation distance, referred to as the source-to-image distance (SID), assists in appropriately controlling the size of the x-ray field during diagnostic use of the imaging system. Further, many regulatory requirements specify that the SID must be clearly displayed to the operator or user of the system with a certain level of accuracy.

Generally, known installation and calibration procedures for establishing fixed SID setpoints and corresponding SID readouts, require the presence of a field engineer who, through a trial and error process, calibrates the radiographic imaging system and installs fixed, preset detent positions that lock the x-ray source into various repeatable separation distances from the detector. For example, the field engineer may install an electromechanical switch, or other device, in the ceiling or the superstructure of the x-ray source that indicates to the user in a tactile or otherwise perceptible manner that the x-ray source is at one of the preset SID positions. Many radiographic imaging systems include industry-standard SID setpoints at separation distances of, for example, 40 inches, 60 inches, and 72 inches.

The installation and calibration procedure, however, becomes even more complex if the detector also is nonstationary. In such event, the field engineer must repeat the setup and calibration procedure at multiple detector positions and install several setpoint or detent devices at the corresponding multiple determined SID positions.

Once the preset SID positions are determined and marked with a detent device, the SID positions are fixed. Thus, a user of the imaging system is not afforded flexibility in the event that the user may desire an SID position that is non-standard. Accordingly, even though either the x-ray source or the x-ray detector could be moved to a variety of different positions such that patients of various sizes could be accommodated or various anatomical parts could be more easily imaged, the actual positions in which the x-ray source could be located with respect to the x-ray detector are restricted to only those few positions which have corresponding fixed detent setpoints.

Preset fixed setpoints can also result in decreased system reliability because the physical switches or detent devices increase the number of components which can potentially fail during system usage.

Thus, it would be desirable to provide a system and method for installing and calibrating a digital radiographic imaging system that would avoid time-consuming iterative procedures for determining fixed SID positions and for providing a calibrated readout and display of the actual SID. It would be further desirable if such a system and method would result in the elimination of, or reduced reliance on, fixed setpoints and physical fixed setpoint devices, thus affording greater flexibility and increasing the reliability of the system.

SUMMARY OF THE INVENTION

The present invention addresses one or more of the shortcomings noted above.

For example, a method for determining a setpoint for setting the separation distance between a radiation source and a digital detector in a digital imaging system includes positioning the radiation source with respect to the detector at a first source position, sensing the first source position and providing a first feedback signal representative thereof, and generating a first radiation beam having a beam angle. The first beam is detected on the detector and the size of the impact area of the first beam is determined. The source is then displaced to a second source position and a feedback signal representative of the position is generated. A second radiation beam having substantially the same beam angle as the first beam is generated while the source is at the second position. The second beam is detected on the detector and a size of the impact area of the second beam is determined. A separation gain constant is then determined based on the displacement of the source and the first and second feedback signals representative of the source positions. A separation distance between the source and the digital detector based on the sizes of the impact areas and the source displacement also is calculated. The separation gain constant and the calculated separation distance can then be utilized to position the radiation source at a selected source-to-image distance (SID).

In another aspect of the present technique, a method for determining a separation distance between a radiation source and a digital detector positioned to detect a radiation beam generated by the source is provided. A first beam is generated with the source positioned at a first source position and a size of a first impact area of the first beam detected on the detector is determined. A system parameter is then varied such that a second radiation beam generated by the source has a second impact area on the detector, the second impact area having a second size that is different from the first size of the first impact area. The second beam is then generated and the second size of the second impact area of the second beam is determined. A first separation distance of the radiation source with respect to the detector is computed based on the determined first and second sizes of the first and second impact areas and the value of the varied system parameter.

DETAILED DESCRIPTION OF THE INVENTION

The following detailed description is made with reference to a digital radiographic imaging system having an x-ray source and a digital detector configured to detect x-ray beams generated by the source. It should be understood, however, that the system and method described hereafter can be implemented in other types of digital imaging systems which have a source that generates radiation other than in the x-ray spectrum (e.g., visible light, infrared, etc.). In such imaging systems, an appropriate digital detector is provided which is configured to detect the particular type of radiation generated by the radiation source.

Figure 1:
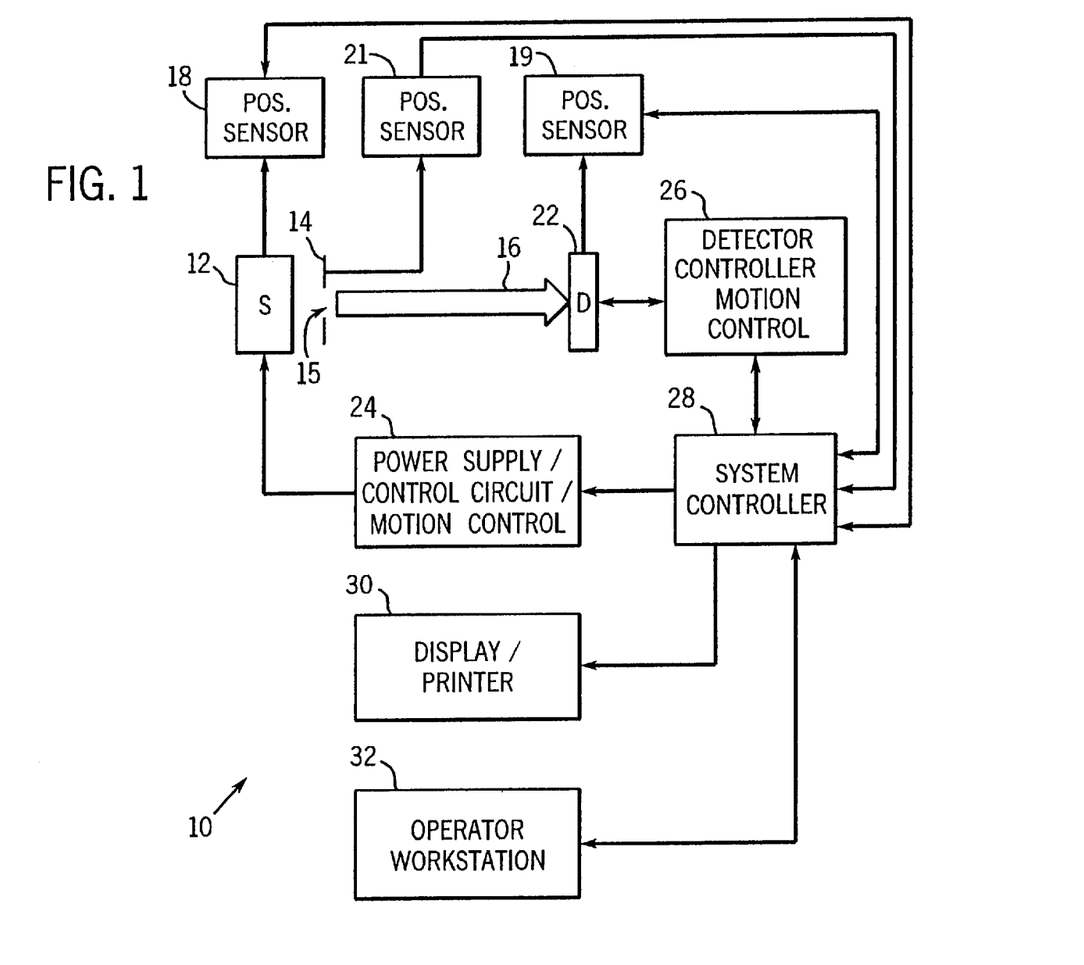
FIG. 1 is a diagrammatical overview of a digital x-ray imaging system in which the present technique is incorporated.

Turning now to the figures, FIG. 1 illustrates diagrammatically an imaging system 10 for acquiring and processing discrete pixel image data. In the illustrated embodiment, system 10 is a digital x-ray system that facilitates installation and calibration procedures such that accurate image data can subsequently be acquired and processed by system 10 for output and display. In the embodiment illustrated in FIG. 1, imaging system 10 includes a source of x-ray radiation 12 having a collimator assembly 14. Source 12 is configured to generate an x-ray beam, referenced generally by the numeral 16, that passes through an opening 15 in collimator assembly 14. Opening 15 in collimator 14 is adjustable (e.g., by adjusting the position of collimator blades (not shown)) such that the size (i.e., the beam angle) of x-ray beam 16 may be varied. After passing through opening 15 in collimator assembly 14, x-ray beam 16 impacts upon and is detected by a digital x-ray detector 22. Detector 22 converts the x-ray photons received on its surface to lower energy photons, and subsequently to electrical signals which are acquired and processed to reconstruct an image.

In an exemplary embodiment, system 10 is located in an examination room. The examination room may include, for example, a horizontal patient positioner or table for positioning a subject, such as a patient, to be imaged. The horizontal table or positioner may include a track disposed along a translational axis (e.g. the longitudinal axis) of the table for moving a detector 22 from one end of the table to another. Movement of detector 22 adds flexibility to system 10, because a movable detector allows various anatomical parts of a subject to be imaged without requiring repositioning of the subject and more easily accommodates patients of various sizes.

The examination room may also include an upright, or vertical, positioner against which a subject, such as a patient, may be positioned. Such an upright positioner may include a track disposed along a translational axis of the positioner such that a detector 22 may be moved between upper and lower vertical positions. Again, such movement advantageously allows accommodation of subjects of different sizes and/or facilitates imaging of different anatomical targets.

In an exemplary embodiment, the examination room includes an x-ray source 12 which is movable in longitudinal, lateral, and vertical directions (as well as about two angular degrees of freedom), such that the source can be positioned to generate an x-ray field that may be detected by a detector 22 associated with a horizontal patient positioner or a detector 22 associated with a vertical positioner. For example, the source 12 may be movable in the longitudinal direction along a track mounted to the ceiling of the examination room or the superstructure which supports the source 12. Such a track generally is positioned such that it is substantially parallel to the track of the horizontal patient positioner along which the detector 22 may be moved. The source 12 may also be movable both laterally and vertically with respect to the longitudinal direction. Further, the source may be arranged to angularly rotate such that the same source may be used in conjunction with either a detector 22 associated with a horizontal positioner or a detector 22 associated with an upright positioner. Accordingly, the mobility of source 12 allows source 12 to be located at any number of positions such that an x-ray beam generated by source 12 can be centered with respect to detector 22 and such that the separation distance between source 12 and detector 22 (i.e., the SID) can be varied.

In the embodiment illustrated in FIG. 1, imaging system 10 further includes a source position transducer 18 to sense and provide an electrical signal representative of the position of the source 12 in the longitudinal, lateral, and/or vertical directions. System 10 further includes a detector position transducer 19 to sense and provide an electrical signal representative of the position of the detector 22 with respect to the translational axis of the horizontal positioner or of the upright positioner. Exemplary position transducers 18 and 19 are continuous position sensors, such as potentiometers, optical encoders, etc. Further, system 10 may include a position sensing transducer 21 to sense the size, or a change in the size, of opening 15 of collimator assembly 14. In an exemplary embodiment, such a position sensing transducer 21, which typically is provided in conventional collimator assemblies, may sense the size of opening 15 by sensing the position of movable collimator blades, which can be adjusted to create openings of different sizes.

Source 12 is controlled by a power supply/control circuit 24 which provides both power and control signals for installation and setup procedures, as well as for examination sequences. In an exemplary embodiment, control circuit 24 may further include positioning or motion control elements, such as motor drive circuitry and a motor, to position the source 12 along any of the longitudinal, lateral, and vertical axes. As further illustrated in FIG. 1, detector 22 is coupled to a detector controller 26, which commands acquisition of the imaging signals generated in the detector. Detector controller 26 may also execute various signal processing and filtration functions, such as for initial adjustment of dynamic ranges, interleaving of digital image data, and so forth. Detector controller 26 may also include positioning or motion control elements, such as motor drive circuitry and a motor, for positioning the detector 22 along the translational axis of the patient positioner.

Both power supply/control circuit 24 and detector controller 26 are responsive to signals from a system controller 28. In general, system controller 28 commands operation of the imaging system to execute installation and calibration procedures, including generation of command signals to control movement and positioning of source 12 and detector 22 and processing of received data and signals to determine system calibration and gain factors. System controller 10 also commands operation of the imaging system to execute examination protocols and to process acquired image data. In the present context, system controller 28 includes signal processing circuitry, typically based upon a general purpose or application-specific digital computer, associated memory circuitry for storing programs and routines executed by the computer, as well as configuration parameters and image data, interface circuits, and so forth. In the embodiment illustrated in FIG. 1, system controller 28 (or other appropriate processing module), in accordance with a stored setup program, receives feedback signals from position transducers 18, 19 and 21, and image data from detector controller 26, and processes the signals and data to determine SIDs and SID setpoints for positioning source 12 with respect to detector 22 and for providing a calibrated readout of the actual SID), as will be explained in detail below.

In the embodiment illustrated in FIG. 1, system controller 28 is also linked to at least one output device, such as a display or printer, as indicated at reference numeral 30. The output device may include standard or special purpose computer monitors and associated processing circuitry. One or more operator workstations 32 may be further linked in the system for outputting system parameters, controlling installation and setup procedures, requesting and controlling the setup of examinations, viewing images, and so forth. In general, displays, printers, workstations, and similar devices supplied within the system may be local to the data acquisition components, such as located physically within the examination room, or may be remote from these components, such as elsewhere within an institution or hospital, or in an entirely different location, linked to the image acquisition system via one or more configurable networks, such as the Internet, virtual private networks, and so forth.

Figure 2:
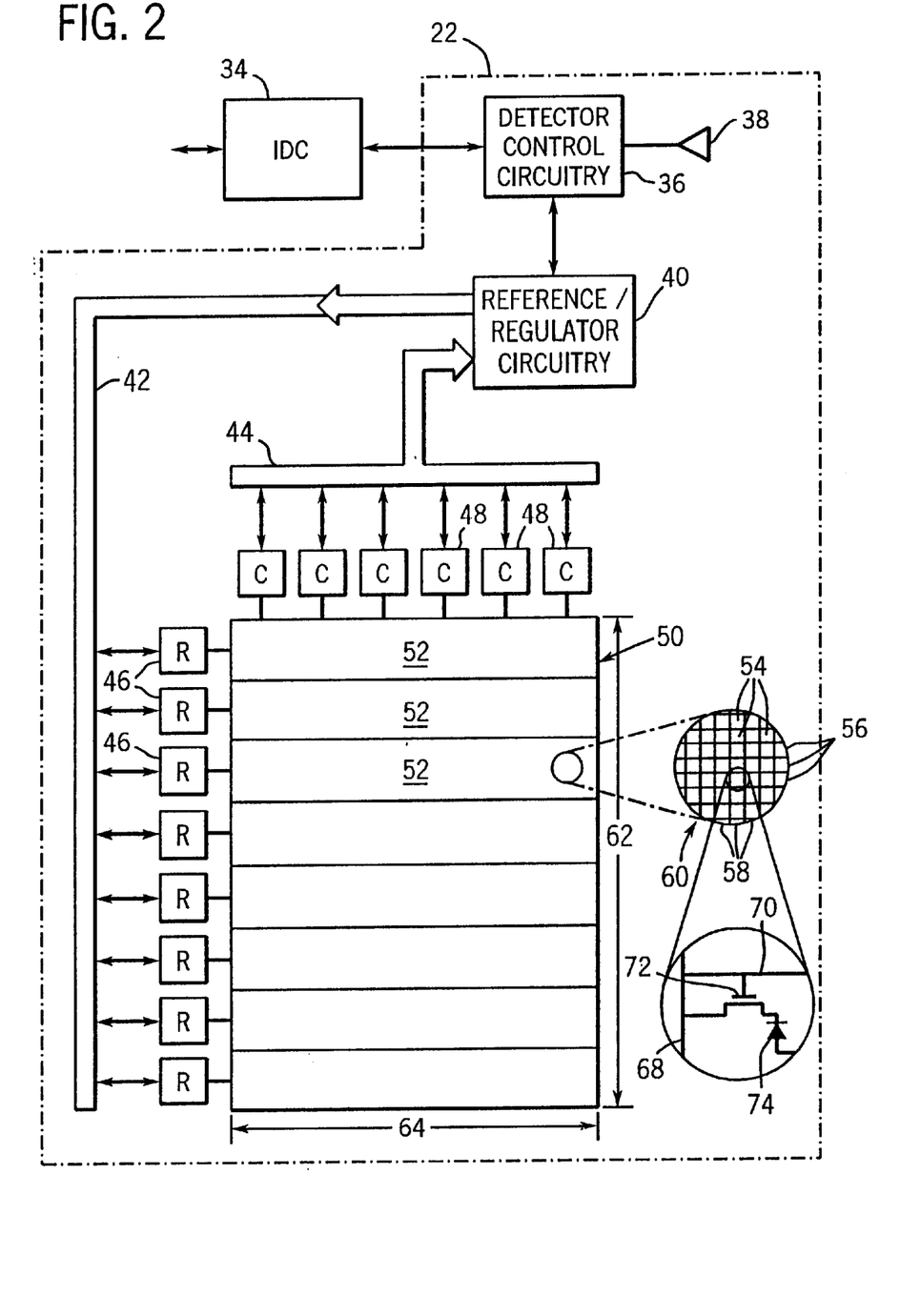
FIG. 2 is a diagrammatical representation of certain of the functional circuitry for producing image data in a detector of the system of FIG. 1.

FIG. 2 is a diagrammatical representation of functional components of an exemplary digital detector 22. FIG. 2 also represents an imaging detector controller or IDC 34 which will typically be configured within detector controller 26. IDC 34 includes a CPU or digital signal processor, as well as memory circuits for commanding acquisition of sensed signals from the detector. IDC 34 is coupled via two-way fiberoptic conductors to detector control circuitry 36 within detector 22. IDC 34 thereby exchanges command signals for image data within the detector during operation.

Detector control circuitry 36 receives DC power from a power source, represented generally at reference numeral 38. Detector control circuitry 36 is configured to originate timing and control commands for row and column drivers used to transmit signals during data acquisition phases of operation of the system. Circuitry 36 therefore transmits power and control signals to reference/regulator circuitry 40 and receives digital image pixel data from circuitry 40.

In the exemplary embodiment illustrated, detector 22 includes a scintillator that converts x-ray photons received on the detector surface during examinations to lower energy (light) photons. An array of photodetectors then converts the light photons to electrical signals which are representative of the number of photons or the intensity of radiation impacting individual pixel regions of the detector surface. Readout electronics convert the resulting analog signals to digital values that can be processed, stored, and displayed, such as in a display 30 or a workstation 32, following reconstruction of the image. In a present form, the array of photodetectors is formed on a single base of amorphous silicon. The array elements are organized in rows and columns, with each element consisting of a photodiode and a thin film transistor. The cathode of each diode is connected to the source of the transistor, and the anodes of all diodes are connected to a negative bias voltage. The gates of the transistors in each row are connected together and the row electrodes are connected to the scanning electronics. The drains of the transistors in a column are connected together and an electrode of each column is connected to readout electronics.

In the embodiment illustrated in FIG. 2, by way of example, a row bus 42 includes a plurality of conductors for enabling readout from various columns of the detector, as well as for disabling rows and applying a charge compensation voltage to selected rows, where desired. A column bus 44 includes additional conductors for commanding readout from the columns while the rows are sequentially enabled. Row bus 42 is coupled to a series of row drivers 46, each of which commands enabling of a series of rows in the detector. Similarly, readout electronics 48 are coupled to column bus 44 for commanding readout of all columns of the detector.

In the illustrated embodiment, row drivers 46 and readout electronics 48 are coupled to a detector panel 50 which may be subdivided into a plurality of sections 52. Each section 52 is coupled to one of the row drivers 46 and includes a number of rows. Similarly, each column driver 48 is coupled to a series of columns. The photodiode and thin film transistor arrangement mentioned above thereby define a series of pixels or discrete picture elements 54 which are arranged in rows 56 and columns 58. The rows and columns define an image matrix 60, having a known height 62, a known width 64, and a known number of rows and columns.

As also illustrated in FIG. 2, each pixel 54 is generally defined at a row and column crossing, at which a column electrode 68 crosses a row electrode 70. As mentioned above, a thin film transistor 72 is provided at each crossing location for each pixel, as is a photodiode 74. As each row is enabled by row drivers 46, signals from each photodiode may be accessed via readout electronics 48, and converted to digital signals for subsequent processing and image reconstruction.

Before imaging system 10 may be used to perform examination sequences, system 10 is properly installed and calibrated to ensure compliance with customer needs, performance requirements, and various regulatory standards. A performance variable established during the setup and calibration process is the SID accuracy of the system 10. The setup of SID involves both the establishment of SID setpoints and the provision of an accurate calibrated readout that is visible to the user and which is representative of the actual physical measurement of the SID. Accurate establishment and calculation of the SID assists in appropriate control of the size of the x-ray field generated during diagnostic use of system 10.

Figure 3:
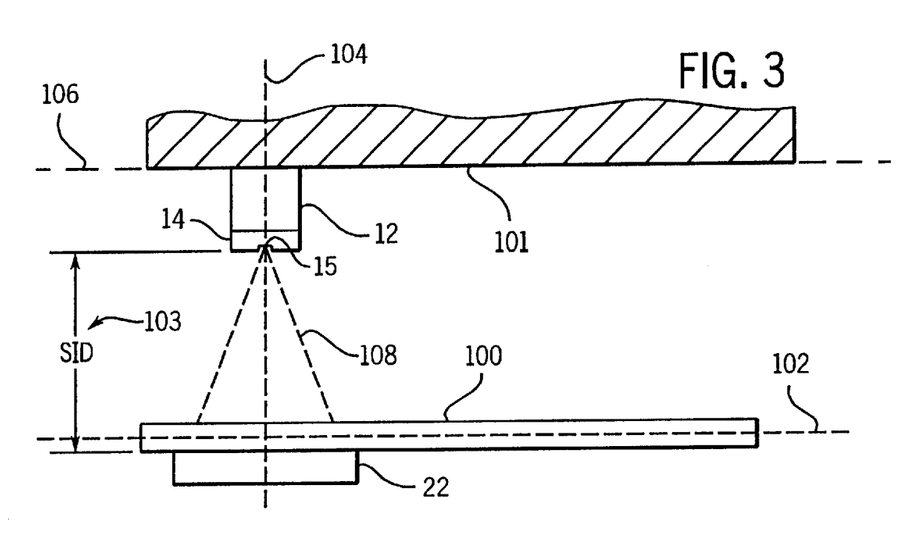
FIG. 3 is a side view of certain of the image acquisition components of the system of FIG. 1, and, in particular, illustrates the orientation of an x-ray source with respect to a digital x-ray detector associated with a patient positioner.
Figure 4:
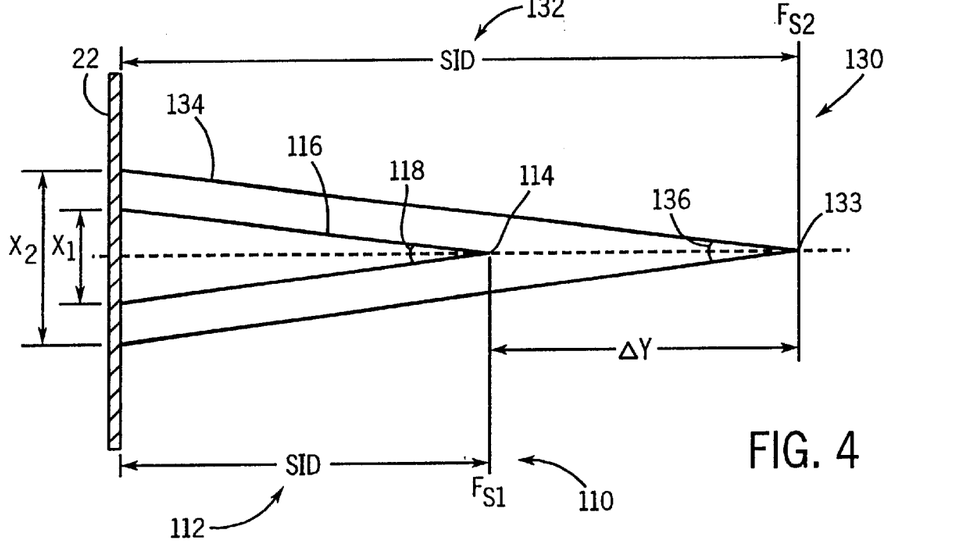
FIG. 4 illustrates an exemplary installation and calibration technique for the digital x-ray imaging system of FIG. 1, in which the x-ray source generates an x-ray beam having a fixed angle while the source is at two different separation distances from the detector.
Figure 4A:
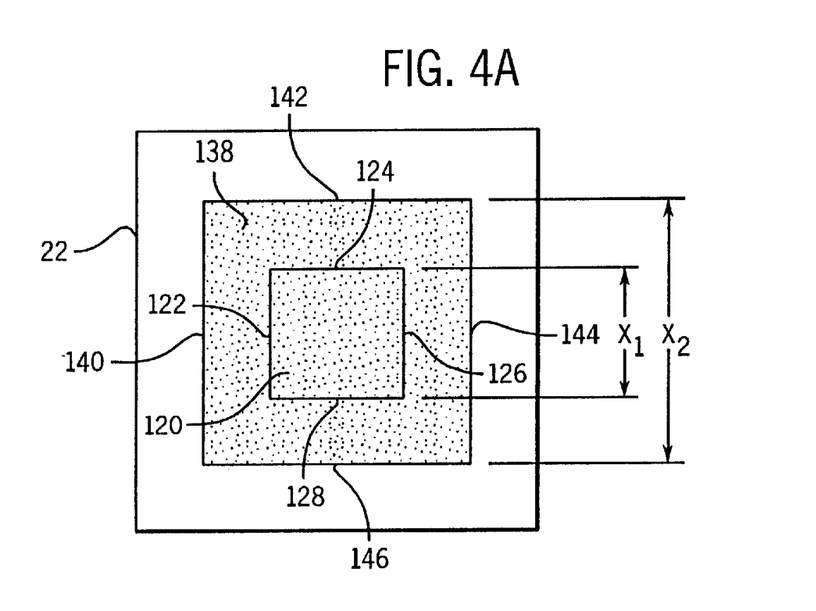
FIG. 4A illustrates the impact areas on the detector of two different x-ray beams which have the same beam angle that were generated while the x-ray source was at two different separation distances from the detector, as illustrated in FIG. 4.

Exemplary techniques for establishing SID setpoints and providing a calibrated SID readout may be understood with reference to FIGS. 3–4A. Turning first to FIG. 3, radiation source 12 is shown movably mounted to a support structure 101 and positioned with respect to detector 22, which is associated with a patient positioner 100. The distance between source 12 and detector 22, i.e. the SID, is referenced generally by the numeral 103. Although the positioner 100 is illustrated in a horizontal orientation, it should be understood that positioner 100 may be either a horizontal positioner, such as a patient table, or an upright positioner. In the exemplary embodiment illustrated in FIG. 3, detector 22 is movable along a detector translational axis 102 and source 12 is movable along source-to-detector axis 104 and source translational axis 106. As further illustrated in FIG. 3, source 12 generates an x-ray beam 108 which impacts upon and is detected by detector 22. The size of beam 108 is determined by the size of opening 15 in collimator assembly 14.

Turning now to FIG. 4, an exemplary technique for establishing SID setpoints for system 10 is illustrated. It should be understood that, although detector 22 is shown in an upright position, the exemplary technique which will be described can also be used with detectors associated with horizontal positioners. The technique illustrated in FIG. 4 involves generating an x-ray beam having a fixed beam angle at two different source positions and detection of the respective x-ray beams at the detector.

As illustrated, source 12 is positioned at a first source position 110 which corresponds to a first SID, which is referenced generally by the numeral 112. Thus, the source-to-image distance 112 is the distance between the detector 22 and focal spot 114 of an x-ray beam 116 generated by source 12 while at the first source position 110. Further, when source 12 is at first source position 110, source position transducer 18 provides a feedback signal, $F_{S1}$, which corresponds to the first source position 110.

As further illustrated in FIG. 4, x-ray beam 116 has a beam angle 118 which is determined by the size of the opening 15 of collimator assembly 14. X-ray beam 116 impacts detector 22 at an impact area 120, which is illustrated in FIG. 4A. Impact area 120 is defined by peripheral edges 122, 124, 126, and 128. Although impact area 120 is illustrated as having a rectangular or square shape, it should be understood that the peripheral edges 122–128 may be curved such that the periphery of impact area 120 is circular or otherwise curvilinear. Detector 22 detects the impact of x-ray beam 116 and generates electrical signals representative of the detected x-ray beam 116. Based on these electrical signals, the size of impact area 120 may be determined by detector controller 26 and system controller 28 in accordance with appropriate algorithms. In an exemplary embodiment, the size of impact area 120 is represented by detecting opposing peripheral edges, e.g., edges 124 and 128, and then determining the distance between the opposing peripheral edges. For example, an algorithm for detecting opposing lateral edges 124 and 128 may include scanning each row of the image matrix of the detector 22 and comparing adjacent scanned rows until a substantial variation between the signals read from adjacent rows is detected. Such a substantial variation may be representative of a peripheral edge of the impact area 120. However, it should be understood that the peripheral edges can be detected in other manners using other appropriate techniques and algorithms, as would be appreciated by one of ordinary skill in the art. Once the rows corresponding to the peripheral edges 124 and 128 are determined, a signal may be provided that corresponds to or represents the distance between peripheral edges 124 and 128.

The size of the impact area 120 measured at detector 22 is related to the source-to-image distance 112 according to the following relationship:

$$\frac{X_1}{2} = Y_1 \tan\phi$$

where $X_1$ represents the size of impact area 120, $Y_1$ represents SID 112, and $\phi$ represents the beam angle 118 of x-ray beam 116.

To continue with the installation and calibration procedure, source 12 is then moved to a second source position 130, which corresponds to a second source-to-image distance, referenced generally by the numeral 132. Thus, SID 132 is the distance between detector 22 and focal spot 133 of an x-ray 134 generated by source 12 while at position 130. Further, while source 12 is at source position 130, source position transducer 18 generates a feedback signal, $F_{S2}$, which corresponds to position 130. X-ray beam 134 has a beam angle 136 which is substantially the same as the beam angle 118. That is, the size of the opening 15 of the collimator 14 is substantially the same as it was when the source 12 was at source position 110. Referring to FIG. 4A, x-ray beam 134 impacts detector 22 at an impact area 138, which is defined by peripheral edges 140, 142, 144 and 146. The size of impact area 138 is then determined in the same manner as described above with respect to impact area 138.

The size of impact area 138 measured at detector 22 is related to SID 132 by the following relationship:

$$\frac{X_2}{2} = Y_2 \tan\phi$$

where $X_2$ represents the size of impact area 138, $Y_2$ represents SID 132, and 100 represents the beam angle 136 of x-ray beam 134.

Because the size of beam angle 136 is the same as beam angle 118, the following relationship between the sizes of impact areas 120 and 138, and SID 112 and 132 can be established:

$$\frac{X_1}{X_2} = \frac{Y_1}{Y_2}$$

The physical measurements for $Y_1$ and $Y_2$ are unknown but are related such that:

$$Y_2 = Y_1 + \Delta Y$$

However, )Y can be determined if the x-ray source 12 is displaced by a known distance. For example, the distance between the first source position 110 and the second source position 130 can be physically measured by a field engineer, may be referenced to machined and measured marks on the superstructure supporting source 12, displaced a known distance under control of the system controller 28 and motion control circuitry 24, or derived/calculated from a source position gain constant representing the relationship between source position and position feedback signals that may be obtained during a setup procedure unrelated to the specific determination of the SID. Once the displacement, )Y, of source 12 is known, a gain constant for system 10 can be computed:

$$Gain = \left(\frac{\Delta Y}{F_{S2} - F_{S1}}\right)$$

where $F_{S2}$ represents the electronic feedback signal from the source position transducer 18 when source 12 is at position 130, and $F_{S1}$ represents the electronic feedback signal from source position transducer 18 when source 12 is at position 110.

Further, the actual spatial position for the SIDs corresponding to the first souce position 110 and the second source position 130 can be calculated as follows:

$$Y_1 = \frac{\Delta Y\left(\frac{X_1}{X_2}\right)}{\left(1 - \frac{X_1}{X_2}\right)}$$

$$Y_2 = \frac{\Delta Y\left(\frac{X_2}{X_1}\right)}{\left(1 - \frac{X_2}{X_1}\right)}$$

where $Y_1$ represents the actual spatial measurement for SID 106, and $Y_2$ represents the actual spatial distance corresponding to SID 126.

If desired, the SID computation can be refined by determining additional data points and averaging the results. For example, $Y_1$ and $Y_2$ can be re-calculated for the first and second source positions using different parameters. In an exemplary embodiment, the initial calculations of $Y_1$ and $Y_2$ are performed by determining the size of the impact areas, $X_1$ and $X_2$, of the beams on the detector by finding the distance between the lateral peripheral edges of the respective impact areas, as described above. Second values for $Y_1$ and $Y_2$ can then be recalculated by determining the size of the impact areas, $X_1$ and $X_2$, based on the distance between the longitudinal peripheral edges of the respective impact areas. The initial and second values for $Y_1$ can then be averaged to provide a more accurate computation of the SID at the first source position 110. Similarly, the initial and second values for $Y_2$ can be averaged to provide a more accurate computation of the SID at the second source position 130. Thus, as can be appreciated by those of skill in the art, the computation and averaging of additional data points can contribute to enhanced accuracy of the SID computation.

Having determined the gain constant and $Y_1$, a feedback signal value corresponding to a general SID setpoint can then be determined using the determined gain constant and the empirical data gathered during the calibration of system 10:

$$F = \left(\frac{Y - Y_1}{Gain}\right) + F_S$$

where F is the computed electronic feedback signal from position sensor 10 for a desired physical SID position Y.

Thus, for example, a user of system 10 may select a desired SID, such as 50 inches, input the desired SID to system controller 28 via operator workstation 32, which then determines the electronic feedback signal that will be generated by source position sensor 18 when source 12 is located at a source position that results in the desired SID. The user of system 10 can then move or command movements of source 12 until the feedback signal from source position sensor 18 corresponds to the computed value for F. In an exemplary embodiment, system 10 provides a visible or audible alarm (e.g., a flashing light, a display on the monitor of the user interface, a beeping sound, etc.) to indicate to the user that source 12 is at a source position corresponding to the selected SID (i.e., when the feedback signal generated by position sensor 18 is substantially equal to the computed value, F, for the selected SID). Alternatively, or in addition to the alarm indication, the system controller 28 can be configured to generate a command signal which causes the motion control circuitry in control circuit 24 to apply a brake that substantially halts further movement of source 12 upon receipt of a feedback signal from position sensor 18 which corresponds to the selected SID.

For the methodology described above, it has been understood that a field engineer is present at the location of system 10 to perform the setup and calibration procedure, including the determination of the variable SID positions and the calibrated SID readout. However, it is contemplated that the installation and calibration procedure can be performed from a location that is remote from source 12 and detector 22. For example, the procedure can be initiated and controlled from a user interface or operator workstation, such as an operator workstation 32, that is coupled to system controller 28 via a network, such as the Internet, a local area network, or a wide area network, etc. Further, it should be understood that source 12 and/or detector 22 can be positioned either manually or with the aid of motion control or motorized elements.

Still further, it should be understood that the determination of gain relationships and laterally centered setpoints described above has been determined by performing one x-ray exposure at each of two source locations and calculating the corresponding data points. It should be understood, however, that the described technique can provide more accurate results by performing additional x-ray exposures at each source location, calculating the corresponding data points, and averaging the results. Still further, additional exposures can be performed at additional source locations and the results can be averaged to enhance accuracy. Moreover, it is contemplated that gain constants and the SID can be determined using other appropriate equations rather than the specific equations set forth above. Such other equations may also have a form other than the linear forms described above, such as a polynomial form, which may contribute to enhanced accuracy of the computed results.

Further, the setup procedure has been described for a digital radiographic imaging system which includes a digital x-ray detector. It should be understood, however, that the setup procedure may be implemented in any digital imaging system having other types digital detectors, such as a detector based on charge coupled device technology. Further, the radiation source in the imaging system need not be an x-ray source, but can generate any type of radiation that is useful in the imaging system and that can be detected by the system's detector.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for determining a source-to-image distance (SID) setpoint between a radiation source and a digital detector in a digital imaging system, the method comprising:

positioning the radiation source with respect to the digital detector at a first source position;

sensing the first source position and providing a first feedback signal representative thereof;

generating a first radiation beam with the radiation source, the first radiation beam having a beam angle;

detecting the first radiation beam on the detector;

determining a first size of a first impact area of the first radiation beam on the detector;

displacing the radiation source to a second source position;

determining an amount of the displacement;

sensing the second source position and providing a second feedback signal representative thereof;

generating a second radiation beam with the radiation source, the second radiation beam having substantially the same beam angle as the first radiation beam;

detecting the second radiation beam on the detector;

determining a second size of a second impact area of the second radiation beam on the detector;

determining a separation gain constant based on the determined amount of the displacement and the first and second feedback signals;

determining a separation distance between the radiation source and the digital detector based on the first and second sizes of the first and second impact areas and the determined amount of the displacement; and utilizing the determined separation gain constant and the determined separation distance to position the radiation source at a selected SID.

2. The method as recited in claim 1, further comprising:

displaying indicia representative of the selected SID.

3. The method as recited in claim 1, further comprising:

continuously sensing positions of the radiation source; and generating feedback signals representative thereof, wherein utilizing the determined separation gain constant and the determined separation distance comprises determining a feedback signal value representative of a source position that corresponds to the selected SID.

4. The method as recited in claim 3, further comprising:

displacing the radiation source until a value of the generated feedback signal is substantially equal to the determined feedback signal value that corresponds to the selected SID.

5. The method as recited in claim 4, further comprising:

providing a command signal to initiate determination of the separation gain constant.

6. The method as recited in claim 5, wherein the command signal is provided from a location remote from the radiation source and the digital detector.

7. The method as recited in claim 5, wherein the command signal includes a control signal to position and displace the radiation source.

8. The method as recited in claim 1, wherein determining the first and second sizes of the first and second impact areas comprises:

detecting opposing lateral peripheral edges of the first impact area; and detecting opposing lateral peripheral edges of the second impact area.

9. The method as recited in claim 8, wherein the digital detector comprises a plurality of rows and a plurality of columns which define an image matrix, and detecting opposing lateral peripheral edges of the first impact area comprises determining first and second rows of the image matrix which correspond to the opposing lateral peripheral edges.

10. The method as recited in claim 8, wherein determining the first and second sizes further comprises:

detecting opposing longitudinal peripheral edges of the first impact area; and detecting opposing longitudinal peripheral edges of the second impact area.

11. The method as recited in claim 10, wherein the radiation source comprises an x-ray source.

12. A method for determining a separation distance between a radiation source and a digital detector positioned to detect an radiation beam generated by the radiation source, the method comprising:

generating a first radiation beam with the radiation source positioned at a first source position;

determining a first size of a first impact area of the first radiation beam detected on the detector;

varying a system parameter such that a second radiation beam generated by the radiation source has a second impact area on the detector, the second impact area having a second size that is different than the first size;

generating the second radiation beam;

determining the second size of the second impact area of the second radiation beam detected on the detector; and calculating a first separation distance of the radiation source with respect to the detector based on the determined first and second sizes of the first and second impact areas and the variation of the system parameter.

13. The method as recited in claim 12, wherein the varied system parameter is a position of the radiation source, and varying the system parameter comprises displacing the radiation source to a second source position displaced from the first source position.

14. The method as recited in claim 13, further comprising:

providing a source position transducer to sense source position and to generate a feedback signal representative of the sensed source position.

15. The method as recited in claim 14, further comprising:

determining a separation gain constant based on the first and second sizes of the first and second impact areas and the feedback signals representative of the first and second source positions;

utilizing the separation gain constant and the calculated first separation distance to position the radiation source at a source position corresponding to a selected source-to-image distance (SID).

16. The method as recited in claim 15, wherein utilizing the separation gain constant and the calculated first separation distance to position the radiation source comprises:

determining a value of feedback signal corresponding to the selected SID; and displacing the radiation source with respect to the detector until the feedback signal generated by the source position transducer is substantially the same as the determined value of feedback signal.

17. The method as recited in claim 16, wherein displacing the radiation source comprises:

providing a command from a remote location to displace the radiation source.

18. The method as recited in claim 12, wherein the first radiation beam has a first beam angle and the system parameter is varied such that the second radiation beam has a second beam angle, the second beam angle being different than The first beam angle of the first radiation beam.

19. The method as recited in claim 18, wherein the first and second radiation beams are generated at the first source position, the first source position corresponding to the calculated first separation distance, and the method further comprises:

providing a source position transducer to detect source position;

generating a feedback signal representative of the detected source position;

displacing the radiation source to a second source position displaced from the first source position;

determining an amount of the displacement;

generating a third radiation beam with the radiation source, the third radiation beam having a third beam angle that is substantially the same as the first beam angle;

determining a third size of a third impact area of the third radiation beam detected on the detector;

determining a separation gain constant based on the determined amount of the displacement and the feedback signals representative of the first and second source positions; and determining a second separation distance between the radiation source and the digital detector based on the sizes of the first and third impact areas and the determined amount of the displacement.

20. The method as recited in claim 19, further comprising:

utilizing the separation gain constant and the determined second separation distance to position the radiation source at a selected SID.

21. The method as recited in claim 20, further comprising:

displaying indicia representative of the selected SID.

22. The method as recited in claim 12, wherein the radiation source comprises an x-ray source.

23. The method as recited in claim 12, wherein determining the sizes of the first and second impact areas comprises:

detecting opposing lateral peripheral edges of the first impact area; and detecting opposing lateral peripheral edges of the second impact area.

24. The method as recited in claim 23, wherein the digital detector comprises a plurality of rows and a plurality of columns which define an image matrix, and detecting the opposing lateral peripheral edges of the first and second impact areas comprises:

determining a row of the image matrix which corresponds to each lateral peripheral edge.

25. The method as recited in claim 12, comprising:

generating a command to initiate computation of the separation distance.

26. The method as recited in claim 25, wherein the command comprises a control signal to vary the system parameter.

27. The method as recited in claim 25, wherein the command is generated from a location remote from the radiation source and the digital detector.

28. A digital imaging system, comprising:

a digital detector;

a radiation source to generate a radiation beam, the radiation source being displaced from the detector and configured to generate a first radiation beam having a first impact area of a first size when detected at the detector and a second radiation beam having a second impact area of a second size when detected at the detector;

a transducer to sense a system parameter and to generate a first feedback signal representative of the system parameter when the radiation source generates the first radiation beam and a second feedback signal representative of the system parameter when the radiation source generates the second radiation beam, wherein a variation of the system parameter causes the second size of the second impact area to be different than the first size of the first impact area; and a processing module configured to:

determine the first size of the first impact area;

determine the second size of the second impact area; and determine a first separation distance of the radiation source with respect to the detector based on the determined first and second sizes and the variation of the system parameter.

29. The system as recited in claim 28, wherein the system parameter is the position of the radiation source and the variation of the system parameter is a displacement of the radiation source with respect to the digital detector, wherein the radiation source is displaced from a first source position to a second source position and the first and second feedback signals are representative of the first and second source positions, respectively.

30. The system as recited in claim 29, wherein the processing module is configured to:

determine a separation gain constant based on the displacement of the radiation source and the first and second feedback signals.

31. The system as recited in claim 30, comprising:

a user interface to input commands and system parameters including a selected separation distance, wherein the processing module is configured to:

utilize the separation gain constant and the determined first separation distance to determine a source position that corresponds to the selected separation distance.

32. The system as recited in claim 31, wherein the user interface is at a location remote from the detector and the source.

33. The system as recited in claim 28, wherein the digital detector comprises a plurality of rows and columns defining an image matrix, and the first size of the first impact area is determined by detecting a pair of rows which correspond to opposing peripheral edges of the first impact area, and the second size of the second impact area is determined by detecting a pair of rows which correspond to opposing peripheral edges of the second impact area.

34. The system as recited in claim 28, wherein the radiation source comprises an x-ray source.

* * * * *